US 6,540,785 B1

(12) United States Patent
Gill et al.

(10) Patent No.: US 6,540,785 B1
(45) Date of Patent: *Apr. 1, 2003

(54) ARTIFICIAL INTERVERTEBRAL JOINT PERMITTING TRANSLATIONAL AND ROTATIONAL MOTION

(75) Inventors: Steven S. Gill, Bristol (GB); Colin Walker, Bristol (GB); James van Hoeck, Cordova, TN (US); Larry Gause, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/534,767

(22) Filed: Mar. 24, 2000

Related U.S. Application Data

(62) Division of application No. 09/177,317, filed on Oct. 22, 1998, now Pat. No. 6,115,637.

(51) Int. Cl.[7] .................................................. A61F 2/44
(52) U.S. Cl. .................................. 623/17.14; 623/17.11; 623/17.15
(58) Field of Search ......................... 623/17.11, 17.14, 623/17.15; 606/99

(56) References Cited

U.S. PATENT DOCUMENTS

| 3,426,364 | A | | 2/1969 | Lumb | |
|---|---|---|---|---|---|
| 3,795,922 | A | | 3/1974 | Herbert et al. | |
| 4,759,766 | A | | 7/1988 | Buettner-Janz et al. | |
| 5,246,458 | A | | 9/1993 | Graham | |
| 5,258,031 | A | * | 11/1993 | Salib et al. | 623/17.15 |
| 5,314,477 | A | | 5/1994 | Marnay | |
| 5,401,269 | A | | 3/1995 | Buttner-Janz | |
| 5,426,773 | A | | 6/1995 | Boyd et al. | |
| 5,507,816 | A | * | 4/1996 | Bullivant | 623/17.15 |
| 5,514,180 | A | | 5/1996 | Heggeness et al. | |
| 5,534,029 | A | | 7/1996 | Shima | |
| 5,556,431 | A | | 9/1996 | Buttner-Janz | |
| 5,562,738 | A | * | 10/1996 | Boyd et al. | 623/17.15 |
| 5,593,445 | A | | 1/1997 | Waits | |
| 5,645,596 | A | | 7/1997 | Kim et al. | |
| 5,645,599 | A | | 7/1997 | Samani | |
| 5,653,762 | A | | 8/1997 | Pisharodi | |
| 5,674,296 | A | | 10/1997 | Bryan et al. | |
| 5,676,701 | A | * | 10/1997 | Yuan et al. | 623/17.15 |
| 5,683,465 | A | * | 11/1997 | Shinn et al. | 623/17.14 |
| 5,755,796 | A | | 5/1998 | Ibo et al. | |
| 5,755,798 | A | | 5/1998 | Papavero et al. | |
| 5,776,196 | A | | 7/1998 | Matsuzaki et al. | |
| 5,782,832 | A | | 7/1998 | Larsen et al. | |
| 5,782,927 | A | | 7/1998 | Klawitter et al. | |
| 5,899,941 | A | * | 5/1999 | Nishijima et al. | 623/17.14 |
| 5,947,971 | A | * | 9/1999 | Kuslich et al. | 606/80 |
| 6,146,421 | A | * | 11/2000 | Gordon et al. | 623/17.15 |
| 6,228,118 | B1 | * | 5/2001 | Gordon | 623/17.14 |

FOREIGN PATENT DOCUMENTS

| EP | 699426 | 3/1996 |
|---|---|---|
| FR | 2718635 | 10/1995 |
| FR | 2737656 | 2/1997 |
| WO | WO 91/13598 | 9/1991 |
| WO | WO 93/10725 | 6/1993 |

* cited by examiner

Primary Examiner—Kevin Shaver
Assistant Examiner—Michael B. Priddy
(74) Attorney, Agent, or Firm—Woodard, Emhardt, Naughton, Moriarty & McNett

(57) ABSTRACT

An intervertebral joint prosthesis having a ball component (22) for engagement with a first vertebra (26) and a trough component (24) for engagement with a second vertebra (27) adjacent to the first vertebra is disclosed. The trough component (24) includes a generally concave surface (50) having a substantially flat portion (52). When the ball component (22) and the trough component (24) are engaged to their respective vertebrae, the ball component (72) and the trough component (24) engage each other, permitting rotation and translation of the vertebrae with respect to each other. Both components include a flange (34,56) for engaging a vertebra. The invention also contemplates a method for and a tool for use in implanting a two-piece intervertebral joint prosthesis.

33 Claims, 7 Drawing Sheets

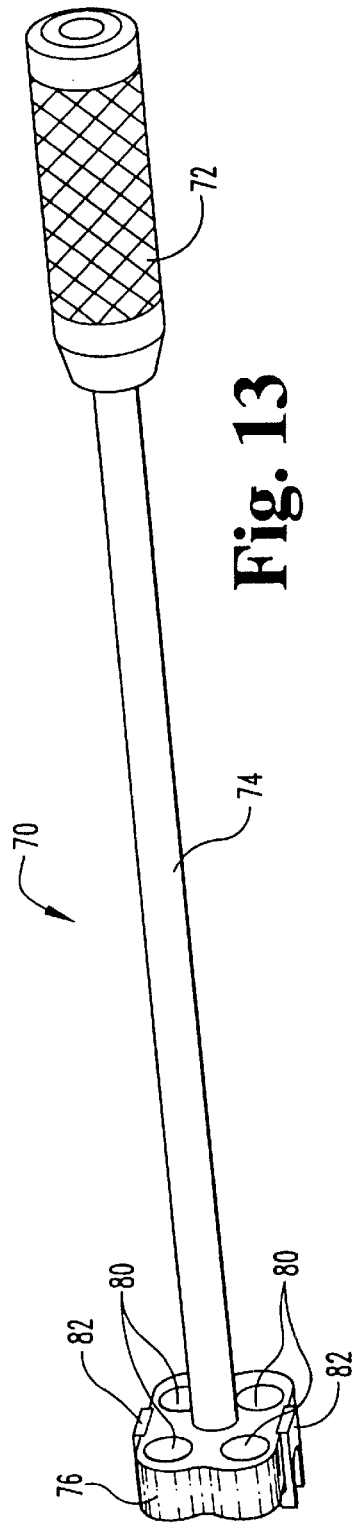
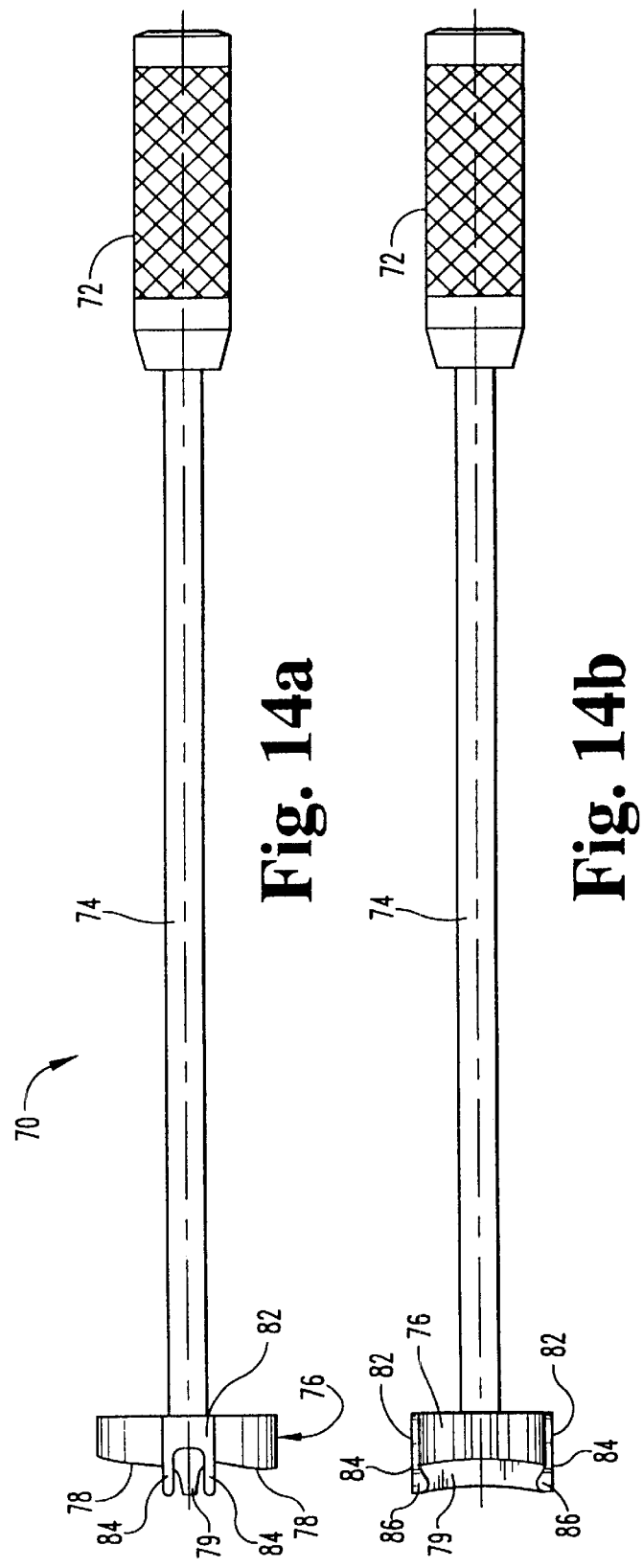

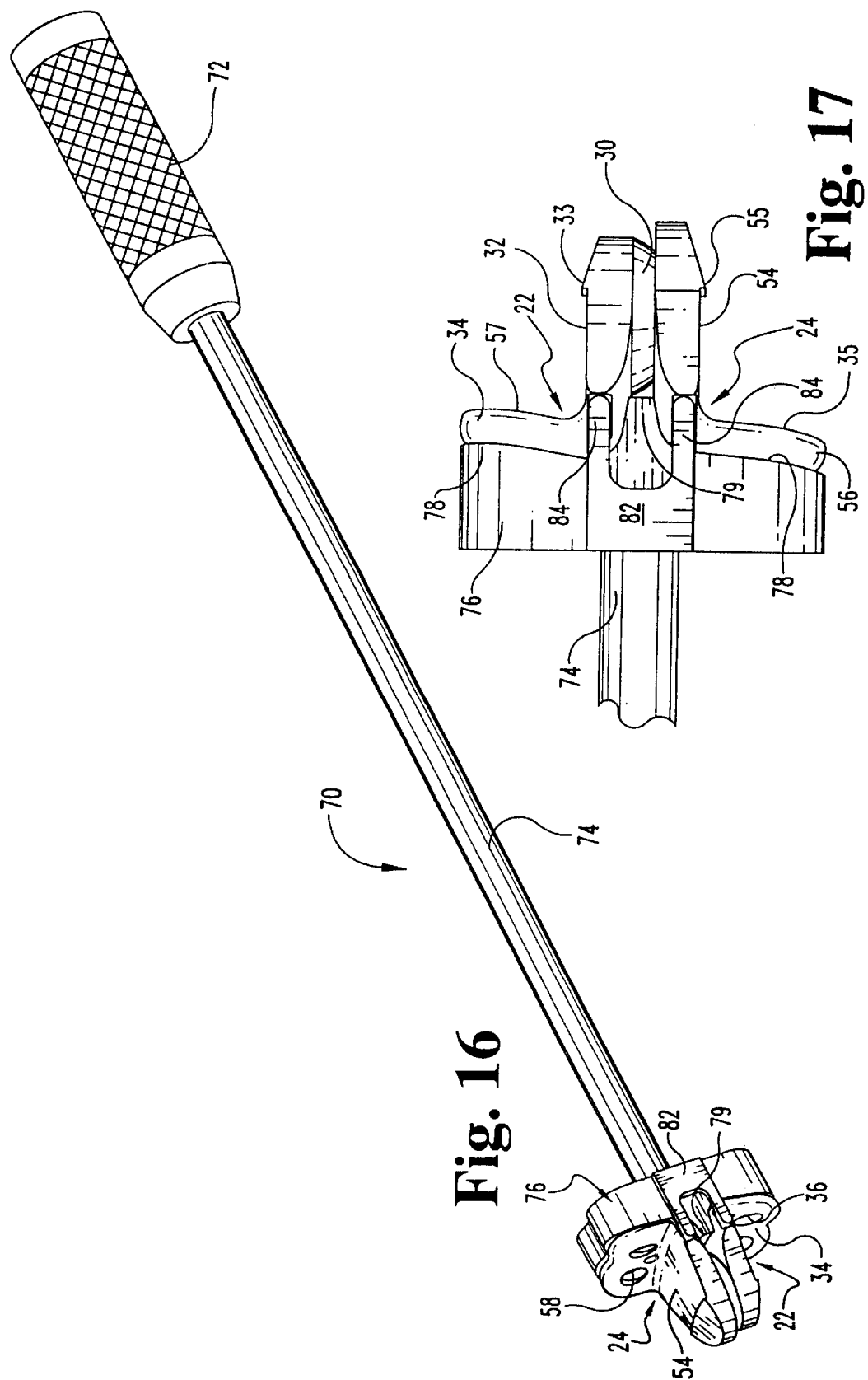

ARTIFICIAL INTERVERTEBRAL JOINT PERMITTING TRANSLATIONAL AND ROTATIONAL MOTION

This is a division of pending U.S. patent application Ser. No. 09/177,317, filed Oct. 22, 1998 now U.S. Pat. No. 6,113,637.

FIELD OF THE INVENTION

The present invention is directed to an intervertebral joint prosthesis. Specifically, the invention includes a device which is implanted in place of degenerated or absent intervertebral disc tissue, and tools and methods for implanting the same.

BACKGROUND OF THE INVENTION

In the treatment of diseases, injuries or malformations affecting spinal motion segments (which include two adjacent vertebrae and the disc tissue or disc space between them), and especially those affecting disc tissue, it has long been known to remove some or all of a degenerated, ruptured or otherwise failing disc. In cases in which intervertebral disc tissue is removed or is otherwise absent from a spinal motion segment, corrective measures are indicated to insure the proper spacing of the vertebrae formerly separated by the removed disc tissue. Commonly, the two vertebrae are fused together using transplanted bone tissue, an artificial fusion element, or other compositions or devices. Fusion of adjacent vertebrae is a procedure that is performed many tens of thousands of times each year in the United States and Canada.

There is increased concern in the spinal medical community, however, that the biomechanical rigidity of the intervertebral fusion may predispose neighboring spinal motion segments to rapid deterioration. See, e.g., B. H. Cummins, J. T. Robertson, and S. S. Gill, Surgical Experience With An Implanted Artificial Cervical Joint, J. Neurosurg. 88:943–948, 1998. For example, removal of the intervertebral disc and subsequent fusion of the C3–C4 vertebrae may spur deterioration of the C2–C3 and C4–C5 segments. A spinal fusion prevents the fused vertebrae from moving rotationally or translationally with respect to each other, as natural disc tissue permits. That lack of mobility may increase the stresses on adjacent spinal motion segments. Follow-up of patients undergoing a successful fusion may reflect an incidence of neighboring segmental disease as high as 20%, and indications are that 50% of fusion patients will continue to have complaints of pain. Several conditions have been found at spinal segments adjacent to a spinal fusion site, including disc degeneration, disc herniation, instability, spinal stenosis, spondylosis and facet joint arthritis. Consequently, many patients may require additional disc removal and/or fusion procedures as a result of a spinal fusion. Alternatives to fusing a spinal motion segment therefore clearly have inherent advantages.

Several different types of intervertebral disc arthroplasty devices have been proposed for preventing collapse of the space between adjacent vertebrae, to reduce pain and to maintain stability and range of rotational motion between the vertebrae. For example, U.S. Pat. No. 5,755,796 discloses a prosthesis for implantation in the disc space between adjacent vertebrae. The prosthesis has two elements, one being attached to the vertebra above the disc space, and the other being attached to the vertebra below the disc space. The lower element includes a hollow box frame having a spherical seat inside, and the upper element includes a spherically-shaped head that fits into the spherical seat. U.S. Pat. No. 5,556,431 discloses a three-piece intervertebral disc endoprosthesis, in which two plates, each having a hollow in one side, are fixed to adjacent vertebrae so that the two hollows face each other across the disc space. The third element is a core having an outwardly rounded surface on each side that fits into the hollows in the vertebral plates. Similarly, U.S. Pat. No. 5,684,296 discloses a prosthesis having two L-shaped members, each having curved sections between which a resilient disc body is placed.

U.S. Pat. Nos. 5,782,832 and 5,683,465 disclose implants having two plate members anchored to adjacent vertebrae within the disc space. In U.S. Pat. No. 5,782,832, the upper plate member has a rounded underside and the lower plate member has a hollowed top side to engage the underside of the upper plate member and allow rotation. In U.S. Pat. No. 5,683,465, the plate members have a snap-fit ball and socket engagement allowing rotation. Other prosthetic intervertebral discs are also known. Some are composite components having metal and rubber or polymer inserts which are designed to replicate the characteristics and performance of the discs in separating and enabling movement of adjacent vertebrae with respect to each other. Other designs are more mechanical in nature, including springs or other damping mechanisms also designed to approximate the behavior of a normal disc.

The normal movement of vertebrae with respect to one another involves variable rotation and translation. These components of the movement are dictated by the shape and size of the individual vertebrae including the relative positions of the unconvertebral joints (in the cervical spine), the orientation of the facet joints and ligamentous constraints. In essence the axis of rotation for any two vertebrae is unique and during flexion or extension will shift, or translate.

The prior art describes disc prosthesis or joints that dictate a fixed axis of rotation that will not permit translation and will therefore prevent normal movement and tend to jam. The latter may lead to excessive stresses on the prosthesis leading to wear or failure or be transferred to adjoining motion segments provoking pain and/or accelerated degeneration.

Further, many prior devices are relatively difficult to implant. Most are designed to be attached via integral anchors to the vertebral surface facing the intervertebral disc space. To implant such a device, the adjacent vertebrae must be spread substantially further apart than their normal distance from each other, so that the prosthesis can be maneuvered between the vertebrae and the anchors can be inserted into their respective vertebrae. Such an operation presents additional risk of injury to the vertebrae themselves from misplacement or scratching by the anchors, and to other tissues due to the spreading of the vertebrae beyond its normal span.

Therefore, there remains a need for an intervertebral joint prosthesis allowing translational as well as rotational movement between implanted vertebrae, and which is easy to implant in a disc space. There is also a need for a method and instrumentation for implanting such an intervertebral joint prosthesis.

SUMMARY OF THE INVENTION

The present invention is directed to an intervertebral joint prosthesis having a ball component for engagement with a first vertebra and a trough component for engagement with a second vertebra adjacent to the first vertebra. The trough component includes a generally concave surface having a substantially flat portion. When the ball component and the trough component are engaged to their respective vertebrae, the ball component and the trough component engage each other in a ball-and-socket relationship permitting rotation and translation with respect to each other. Both the ball component and the trough component include a flange at one end of the component for engaging a vertebra.

The ball component includes a substantially spherically shaped convex portion which engages a substantially spherically shaped concave portion of the trough component, which concave portion also includes a flat portion. In one embodiment, the flanges of each component include holes through which bone screws can be fitted to attach the components to their respective vertebrae. The flanges may be configured to conform to the general shape of the human vertebrae.

By permitting the ball component to slide or translate in the trough component the present invention enables both the axis of rotation and the degree of translation of the joint to be dictated by the anatomical constraints of the motion segment within an acceptable range.

The invention also contemplates a tool for use in implanting an intervertebral joint prosthesis, having an elongated handle portion and a prosthesis-engaging portion having elements which hold the one or more parts of the intervertebral joint prosthesis. In one embodiment, the prosthesis-engaging portion of the tool includes a central flange and/or a surface configured so that the intervertebral prosthesis or its parts are maintained in a predetermined orientation or spatial relationship. Where the intervertebral joint prosthesis includes apertures for accommodating bone screws, the prosthesis-engaging portion of the tool preferably includes associated apertures for drilling holes for bone screws and/or for holding the prosthesis to the tool.

The present invention also encompasses methodology for implanting a two-part intervertebral joint prosthesis which includes placing the prosthesis parts in a predetermined spatial relationship, inserting the parts into a disc space between two adjacent vertebrae so that one of the prosthesis parts abuts one of the vertebrae and the other of the prosthesis parts abuts the other of the vertebrae and so that the predetermined spatial relationship of the prosthesis parts is maintained, and fastening the parts to their respective vertebrae. Particular embodiments of the methodology include connecting the parts to an insertion tool in a predetermined relationship with each other, inserting the insertion tool into the body so that a portion of both parts of the prosthesis are in a disc space between adjacent vertebrae, and fastening each part of the prosthesis to a respective vertebra. A preferred embodiment of the fastening step includes drilling holes in the vertebrae through apertures in the prosthesis parts and a connected insertion tool and threading screws through the apertures and into the bone.

The present invention provides an intervertebral joint prosthesis, and tools and methods for implantation, which allows a normal range of translation and rotation between the adjacent vertebrae to which the prosthesis has been fastened. The prosthesis is easy to implant via its flanges, obviating the need for distention of the adjacent vertebrae to widen the disc space. The intervertebral joint prosthesis is also implanted with a predetermined orientation of the prosthesis or spatial relationship between its components, which reduces or eliminates the need for in vivo adjustment. The prosthesis of the present invention also has a low profile and a minimal number of parts. These and other advantages will be clear to one of ordinary skill in the art by reference to the drawings and to the detailed description herein.

BRIEF DESCRIPTION OF THE DRAWINGS

FIG. 13 is a perspective view of one embodiment of the insertion tool of the present invention.

FIG. 14a is a side view of the embodiment of the insertion tool illustrated in FIG. 13.

FIG. 14b is a top view of the embodiment of the insertion tool illustrated in FIG. 13, rotated 90 degrees around the longitudinal axis illustrated in FIG. 14a.

FIG. 15b is a perspective view of one embodiment of the prosthesis of the present invention engaged to the prosthesis engaging portion of the embodiment of the insertion tool illustrated in FIG. 15a.

FIG. 16 is a perspective view of an embodiment of the prosthesis of the present invention engaged with the insertion tool illustrated in FIG. 13.

FIG. 17 is a side elevational view of an embodiment of the prosthesis of the present invention engaged with an embodiment of the prosthesis engaging surface of the insertion tool illustrated in FIG. 13.

DESCRIPTION OF THE PREFERRED EMBODIMENT

Figures 1, 1A:
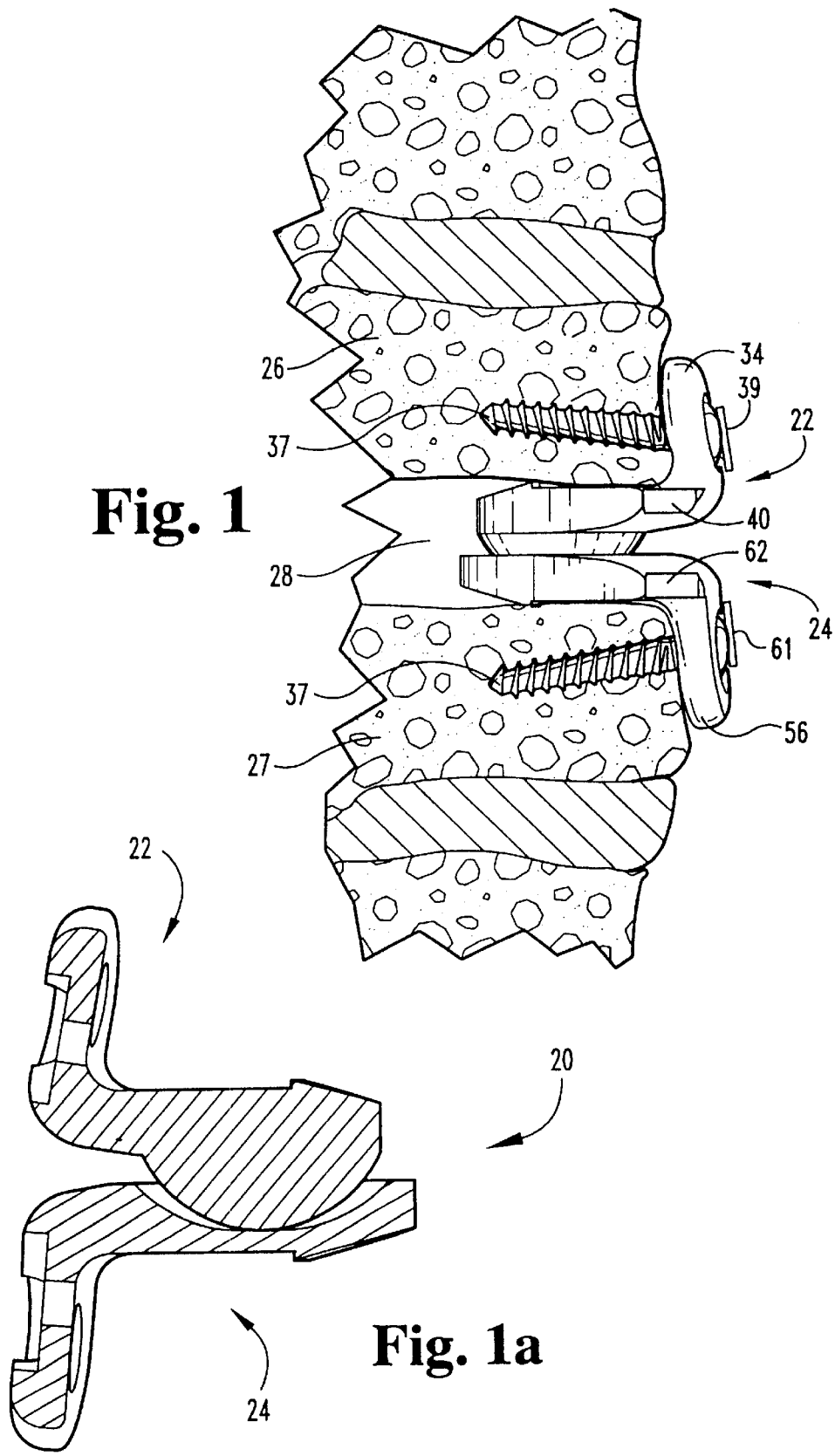
FIG. 1 is a partial sectional view, showing a side view of one embodiment of the prosthesis of the present invention implanted between adjacent vertebrae shown in cross-section.
FIG. 1a is a sectional view of the embodiment of the prosthesis illustrated in FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring generally to FIGS. 1–12, there is shown one embodiment of the intervertebral joint prosthesis 20 of the present invention. Prosthesis 20 includes a ball component 22 and a trough component 24 that are interengagable to form prosthesis 20. In an intervertebral disc space 28 between two adjacent vertebrae 26, 27, ball component 22 is fixed to one of the adjacent vertebrae (e.g. vertebra 26 in FIG. 1), and trough component 24 is fixed to the other adjacent vertebra (e.g. vertebra 27 in FIG. 1) so that the components are interengaged within at least a portion of intervertebral space 28.

Ball component 22 includes a generally convex surface 30 and in one embodiment an opposite substantially flat vertebra engaging surface 32. In a particular embodiment generally convex surface 30 is substantially spherical in shape. In a specific embodiment, a wedge surface 33 is provided at one end of vertebra engaging surface 32, which allows easier insertion of ball component 22 into the disc space and impedes migration of ball component 22. A flange 34 is provided at one end of ball component 22 for attaching ball component 22 to a vertebra, and is preferably formed to have a low profile and bulk. In the embodiment in which ball component 22 includes wedge surface 33, flange 34 is at the opposite end of ball component 22 from wedge surface 33. Flange 34 includes a vertebra engaging surface 35.

In a particular embodiment of ball component 22, flange 34 includes one or more bone screw apertures 36, and in a specific embodiment, two bone screw apertures 36 are provided in a symmetric relationship through flange 34. In that specific embodiment, one or more bone screws 37 (FIG. 4) are threaded into the vertebra through one or more apertures 36 to fix ball component 22 to the vertebra. In the illustrated embodiment, an aperture 38 (FIGS. 2–3) is also provided through flange 34 for a locking screw 39 (FIG. 1). After ball component 22 is attached to the vertebrae using bone screw(s) 37, locking screw 39 is threaded into locking screw aperture 38 in flange 34, covering the heads of bone screw(s) 37 and preventing loosening of bone screw(s) 37 with respect to ball component 22. Additionally, the illustrated embodiment of ball component 22 includes indentations 40 for gripping ball component 22 by an insertion tool, as will be described further hereinafter. Preferably, indentations 40 are located at the base of flange 34, where flange 34 meets substantially flat vertebra engaging surface 32.

Figure 3:
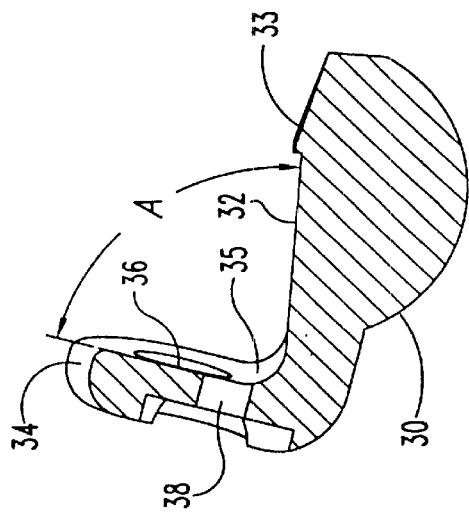
FIG. 3 is a sectional view of the ball component illustrated in FIG. 2, taken along the line 3—3 and viewed in the direction of the arrows.
Figure 4:
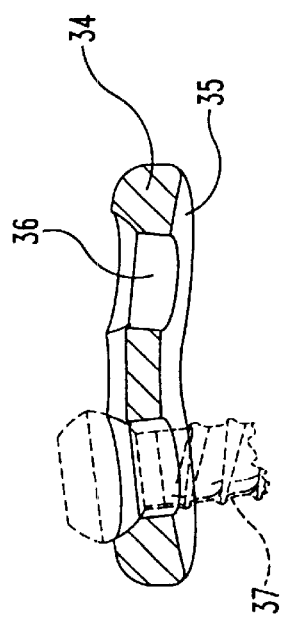
FIG. 4 is a sectional view of the ball component illustrated in FIG. 2, taken along the line 4—4 and viewed in the direction of the arrows.

Flange 34 may be angled with respect to vertebra engaging surface 32 of ball component 22. In a particularly preferred embodiment, as illustrated in FIG. 3, the internal angle A between vertebra engaging surface 35 and vertebra engaging surface 32 is approximately 80 degrees. This angle has been found to provide a good fit with the anterior portion of the upper vertebra in a middle or lower cervical spinal motion segment, such as C4–C5. Ball component 22 can be constructed with a different angle between vertebra engaging surfaces 35 and 32 according to the vertebrae to be implanted and the needs of patients. For example, for upper cervical spinal motion segments such as C2–C3, the internal angle between vertebra engaging surface 35 and vertebra engaging surface 32 may be somewhat more acute, in the range of 70–80 degrees. Flange 34 may also be slightly curved from side to side, as illustrated in FIG. 4. Such curvature is particularly useful for anterior placement of prosthesis 20, as it approximates the lateral curvature of the anterior surface of the human vertebra.

Figure 5:
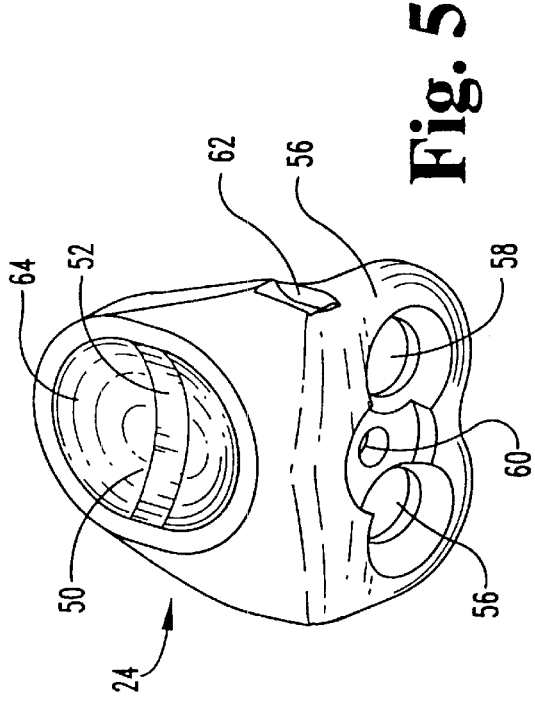
FIG. 5 is a perspective view of an embodiment of the trough component of the prosthesis illustrated in FIG. 1.
Figure 2:
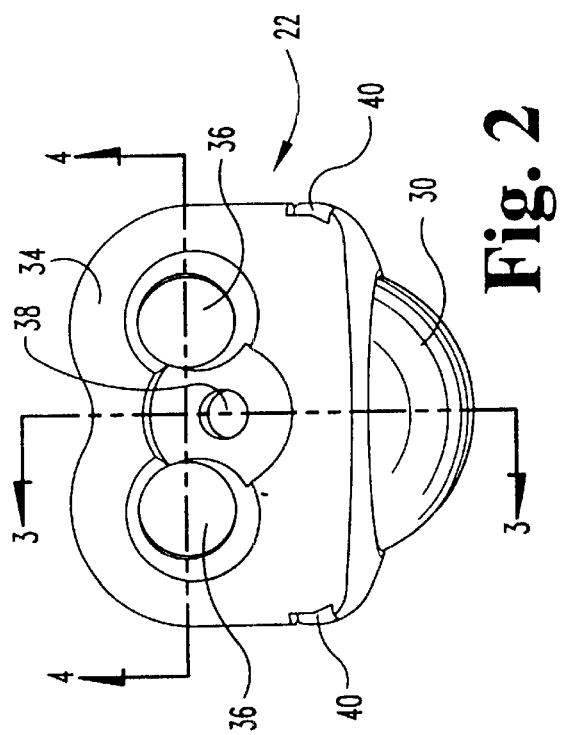
FIG. 2 is a front elevational view of an embodiment of the ball component of the prosthesis illustrated in FIG. 1.
Figure 6:
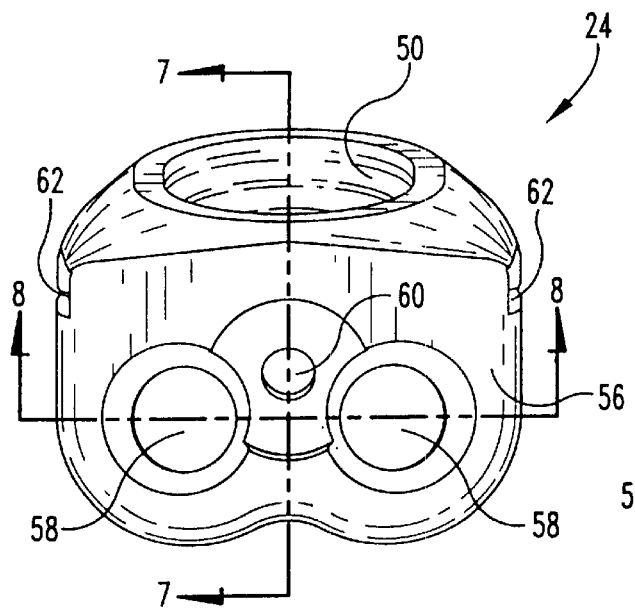
FIG. 6 is a front elevational view of an embodiment of the trough component of the prosthesis illustrated in FIG. 1.
Figure 7:
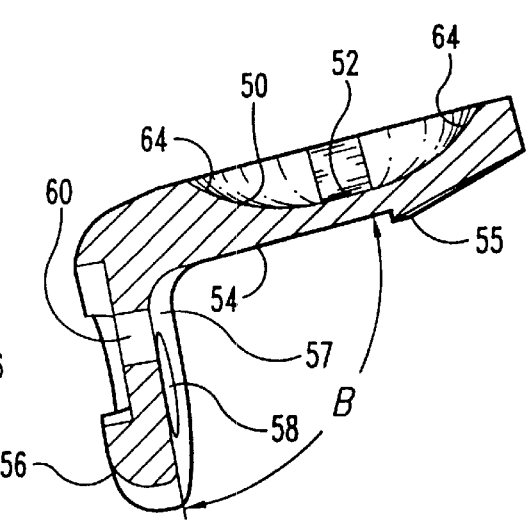
FIG. 7 is a sectional view of the trough component illustrated in FIG. 5, taken along the line 7—7 in FIG. 6 and viewed in the direction of the arrows.

Trough component 24, in the embodiment illustrated, is similar in many respects to ball component 22. Trough component 24 includes a generally concave surface 50, which generally concave surface 50 includes a substantially flat portion 52 (FIGS. 5–7). Opposite generally concave surface 50 is a vertebra engaging surface 54, which, in the illustrated embodiment, includes a wedge surface 55 similar to wedge surface 33 of ball component 22. Trough component 24 also includes a flange 56 and a flange vertebrae engaging surface 57 which are similar to flange 34 and flange vertebra engaging surface 35 of ball component 22.

Figure 8:
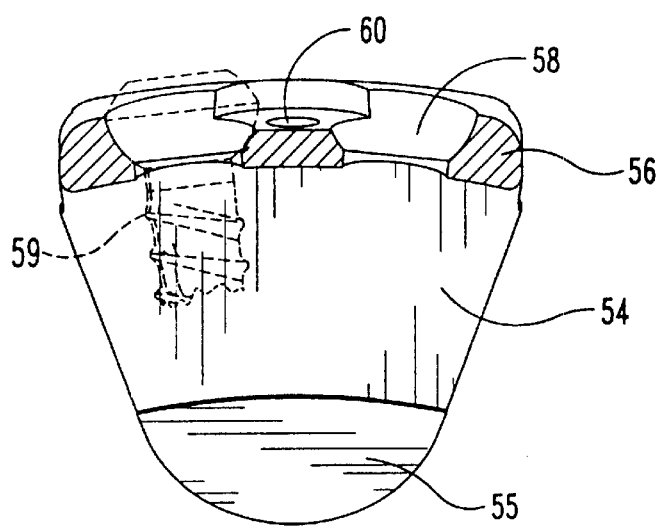
FIG. 8 is a sectional view of the trough component illustrated in FIG. 5, taken along the line 8—8 in FIG. 6 and viewed in the direction of the arrows.

As with a particular embodiment of ball component 22, the illustrated embodiment of flange 56 of trough component 24 includes at least one aperture 58 and preferably two symmetric apertures 58, each of which can accommodate a bone screw 59 (FIG. 8). In that embodiment, flange 56 may also include a lock screw aperture 60 and lock screw 61, as described with respect to ball component 22. Additionally, trough component 24 in one embodiment includes indentations 62, which are similar in location and structure to indentations 40 of ball component 22. Flange 56 of trough component 24, in a preferred embodiment, is also angled with respect to vertebra engaging surface 54. In the illustrated embodiment, the internal angle B between flange vertebra engaging surface 57 and vertebra engaging surface 54 is approximately 95 degrees, which provides a good fit with the anterior portion of a lower vertebra of a middle or lower cervical spinal motion segment. As noted with respect to ball component 22, trough component 24 may be manufactured with a different angle between surfaces 57 and 54 according to the needs of the patient or other factors. For example, for upper cervical spinal motion segments, the angle between surfaces 57 and 54 may be between 90 and 100 degrees.

Figure 10:
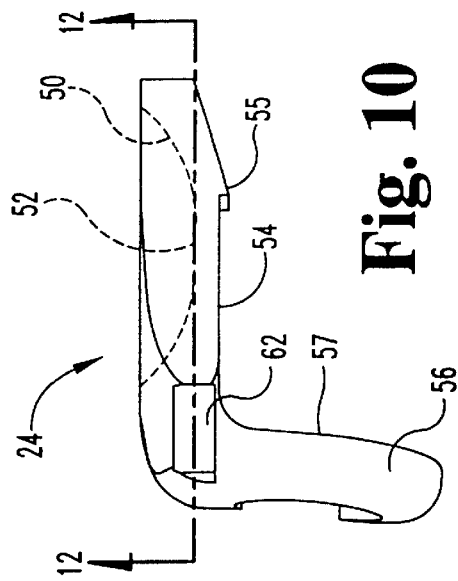
FIG. 10 is a side elevational view of an embodiment of the trough component illustrated in FIG. 5.
Figure 12:
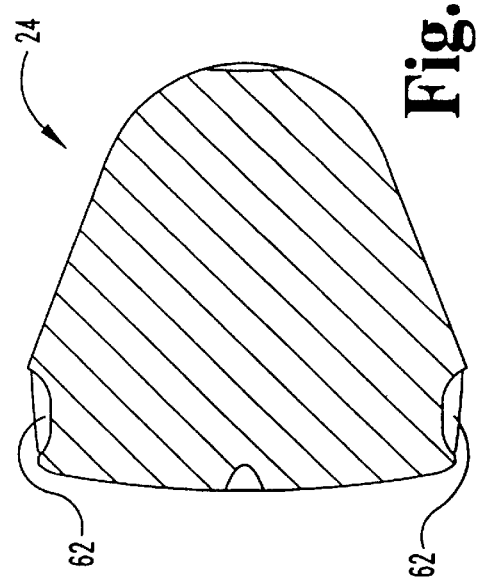
FIG. 12 is a sectional view of the trough component illustrated in FIG. 10, taken along the line 12—12 and viewed in the direction of the arrows.
Figure 9:
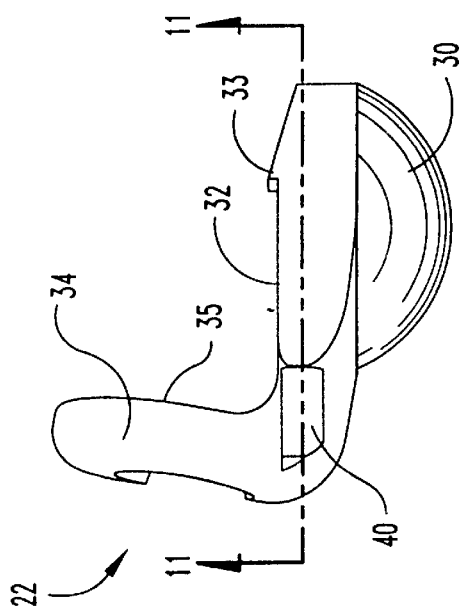
FIG. 9 is a side elevational view of an embodiment of the ball component illustrated in FIG. 2.
Figure 11:
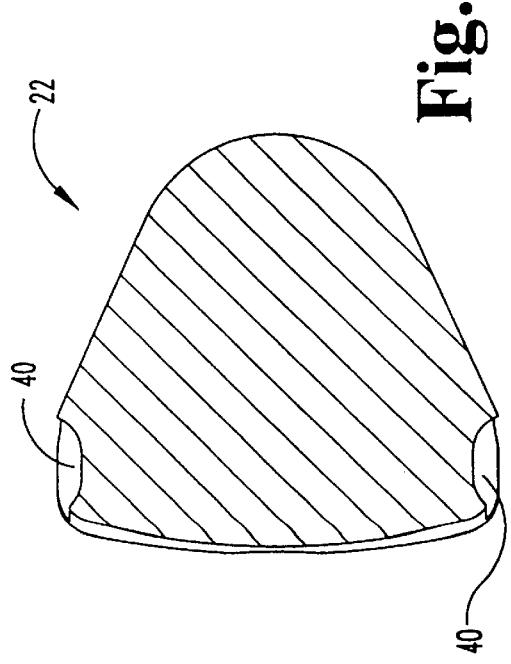
FIG. 11 is a sectional view of the ball component illustrated in FIG. 9, taken along the line 11—11 and viewed in the direction of the arrows.
Figure 15A:
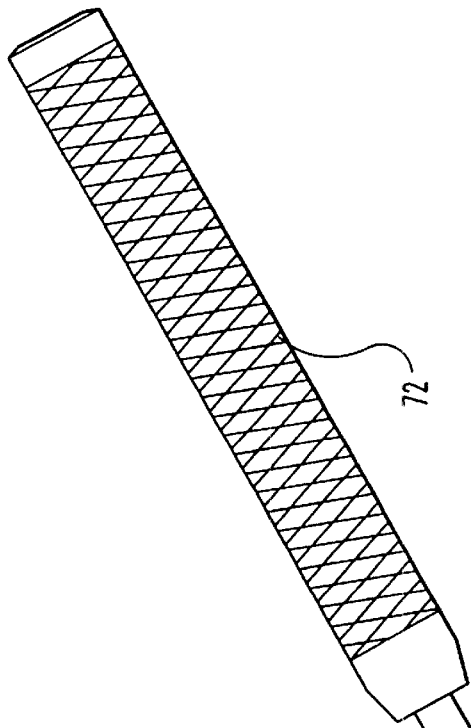
FIG. 15a is a side view of an alternate embodiment of the insertion tool of the present invention.
Figure 15B:
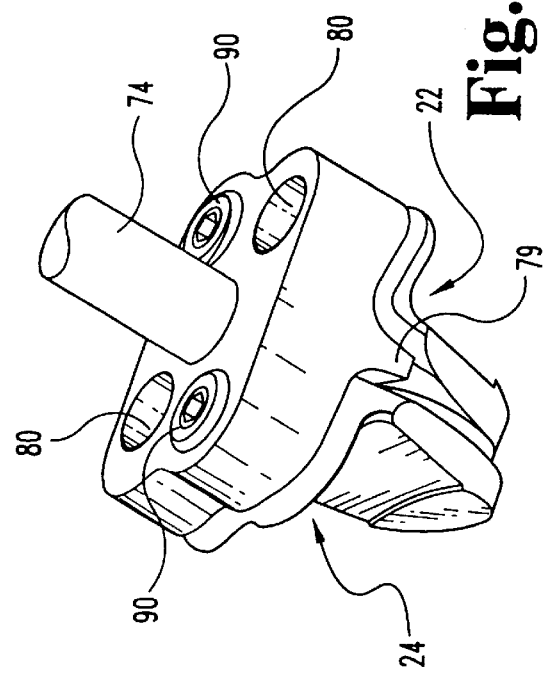

Referring now to FIGS. 5, 7 and 10, the generally concave surface 50 of trough component 24 is illustrated according to one embodiment of the present invention. Generally concave surface 50, in this embodiment, includes a substantially flat (in that it is cylindrical rather than spherical) surface 52 that is approximately centrally located on generally concave surface 50. In a specific embodiment, generally concave surface 50 includes substantially spherical surfaces 64 on both sides of substantially flat surface 52. Substantially flat surface 52 may be of any desired geometrical configuration, though in a currently preferred embodiment, substantially flat surface 52 is in the shape of a rectangle, analogous to a slot in generally concave surface 50, and is approximately parallel to flange 56. In a particular preferred embodiment of ball component 22 and trough component 24, the radius of generally convex surface 30 and of the spherical portion of generally concave surface 50 is approximately the same.

In use, ball component 22 and trough component 24 are attached to adjacent vertebrae so that a portion of components 22, 24 are within the disc space and engage each other to provide a ball-and-socket arrangement which permits rotation and translation of the components, and thereby the vertebrae to which they are fixed with respect to each other. To accomplish that, when prosthesis 20 is implanted generally convex surface 30 of ball component 22 engages generally concave surface 50 of trough component 24. When engaged with generally concave surface 50, generally convex surface 30 can rotate in any direction. When generally convex surface 30 is in contact with substantially flat portion 52 of generally concave surface 50, generally convex surface 30 can move along substantially flat portion 52 in translation, as well as rotate with respect to generally concave surface 50. In a specific embodiment of prosthesis 20, ball component 22 is an "upper" component and is fixed to the vertebra immediately above or superior to the disc space (i.e. the vertebra closer to the head). In that embodiment, trough component 24 is attached to the lower or inferior vertebra (i.e. the vertebra closer to the coccyx). Thus, with ball component 22 attached to one vertebra and trough component 24 attached to an adjacent vertebra so that generally convex surface 30 and generally concave surface 50 are engaged, prosthesis 20 permits the adjacent vertebrae to rotate and translate with respect to each other, providing a normal range of intervertebral joint motion.

The present invention also comprehends an insertion tool 70 for use in implanting joint prosthesis 20. As illustrated in FIGS. 13–17, insertion tool 70 in one embodiment includes an elongated handle portion 72 integral with or attached to an extension portion 74. A prosthesis-engaging portion 76 is attached at the end of extension portion 74. Prosthesis-engaging portion 76 includes prosthesis-engaging surface 78. Prosthesis-engaging surface 78, in the illustrated embodiment, includes a central separator flange 79. The illustrated embodiment of prosthesis-engaging portion 76 also includes a set of apertures 80. This embodiment of insertion tool 70 is intended for use with the embodiment of ball component 22 and trough component 24 having bone screw aperture(s) 36 and 58, respectively, and apertures 80 of prosthesis-engaging portion 76 are configured so as to communicate with aperture(s) 36 of ball component 22 and aperture(s) 58 of trough component 24. In that embodiment, apertures 80 are sized slightly larger than the head(s) of bone screw(s) 37, so that screw(s) 37 may be inserted through apertures 80 to fix components 22 and 24 of prosthesis 20 to their respective vertebrae without also fixing tool 70 thereto.

Prosthesis-engaging portion 76 of insertion tool 70 is also capable of retaining prosthesis 20 in engagement with prosthesis-engaging portion 76. The illustrated embodiment of prosthesis-engaging portion 76 also includes a pair of clips 82 on both sides of prosthesis-engaging portion 76. Clips 82 are designed to hold the embodiments of ball component 22 and trough component 24 that include indentations 40 and 62, respectively. Each clip 82 is attached to prosthesis engaging portion 76, and includes two clip fingers 84 each having a thickened portion 86 for insertion into indentations 40 of ball component 22 and indentations 62 of trough component 24. In an alternative embodiment of insertion tool 70 (FIGS. 15a–15b), prosthesis-engaging portion 76 is provided with apertures 80, and a pair of cam screws 90 which extend through one aperture 80 on each side of separator flange 79. Ball component 22 and trough component 24, in the embodiment in which they include bone screw apertures 36 and 58, respectively, are engaged to prosthesis engaging surface 78 so that apertures 36 and 58 communicate with apertures 80 of prosthesis engaging portion 76. Cam screws 90 are then inserted into one of apertures 36 and one of apertures 58 to lock ball component 22 and trough component 24 to prosthesis engagement surface 76.

As illustrated in FIGS. 14a–17, a particular embodiment of prosthesis-engaging portion 76 is configured to maintain ball component 22 and trough component 24 in a predetermined spatial relationship or neutral position so as to insure correct alignment and positioning of the components with respect to each other and with respect to disc space and vertebrae into which they are to be implanted. Separator flange 79 of prosthesis engaging portion 76 is configured to fit between and to insure the proper spacing between ball component 22 and trough component 24. Prosthesis-engaging surface 78 is angled so that, in cooperation with separator flange 79, prosthesis-engaging portion 76 holds ball component 22 and trough component 24 in a precise predetermined spatial relationship with each other. For example, in the embodiments described above in which vertebra engaging surfaces 32 and 35 of ball component 22 have an internal angle of 80 degrees, prosthesis engaging surface 78 will include a portion forming an internal angle of approximately 80 degrees with separator flange 79. Similarly, in the embodiment of trough component 24 in which vertebra engaging surfaces 54 and 57 have an internal angle of approximately 95 degrees, prosthesis engaging surface 78 will include a portion which forms an internal angle of approximately 95 degrees with separator flange 79. Ball component 22 and trough component 24 are thereby held for implantation together such that vertebra engaging surface 32 of ball component 22 and vertebra engaging surface 54 of trough component 24 are approximately parallel, and such that convex surface 30 is engaged with concave surface 50.

Insertion tool 70 has been described above primarily with respect to the embodiments of prosthesis 20 described herein. Nonetheless, one of ordinary skill in the art will appreciate that insertion tool 70 may be useful with other prostheses that must be held in a particular predetermined orientation, or that have parts that must be retained in a particular spatial relationship.

After an intervertebral disc is resected and/or the disc space is prepared, the intervertebral joint prosthesis 20 of the present invention may be implanted. Ball component 22 and trough component 24 of joint prosthesis 20 are placed in a predetermined relationship with each other, preferably by engagement to insertion tool 70 of the present invention or an equivalent tool. Components 22 and 24, held in a predetermined spatial relationship, are then inserted into the body so that vertebra engaging surfaces 32 and 54 are within the disc space. In the embodiments of components 22 and 24 that include a wedge surface 33 and 55, respectively, wedge surfaces 33 and 55 enable easier implantation of prosthesis 20 by forcing the adjacent vertebrae apart slightly, if necessary, as components 22 and 24 are advanced into the disc space. Once components 22 and 24 are inserted into the disc space, wedge surfaces 33 and 55 grip their respective vertebrae to impede or prevent migration of prosthesis 20.

When prosthesis 20 is in place between the vertebrae, components 22 and 24 are attached to the vertebrae, in one embodiment via flanges 34 and 56. In the embodiment of the present invention in which flanges 34 and 56 include bone screw apertures 36 and 58, respectively, attachment of the components 22 and 24 to the vertebrae may be accomplished by drilling through apertures 36 and 58 into the vertebrae. The drill is then removed and bone screws are threaded into the vertebrae through apertures 36 and 58, thereby fixing components 22 and 24 to their respective vertebrae. When all holes have been drilled and all screws 37 have been threaded into the vertebrae, insertion tool 70 is removed (if one has been used), locking screws may be threaded into apertures 38 and 60 (if present in components 22 and 24), and the operation is concluded.

A specific embodiment of the method of implanting the joint prosthesis 20 includes use of an embodiment of insertion tool 70. In the method using the embodiment of insertion tool 70 having four apertures 80 and a clip 82 on both sides of prosthesis engaging portion 76, components 22 and 24 of joint prosthesis 20 are engaged to insertion tool 70 in a predetermined spatial relationship as described above. Insertion tool 70 is inserted into the body so that joint prosthesis 20 is in the disc space between adjacent vertebrae. A drill (and a drill sleeve, if necessary) is inserted through an aperture 80 in prosthesis engaging portion 76 and through an. aperture 36 or 58 of component 22 or component 24 communicating with the aperture 80, and a hole is drilled in the underlying vertebra. The drilling procedure is repeated for each of the apertures 80 in prosthesis engaging portion 76 which communicate with an aperture 36 or 58 in ball component 22 or trough component 24, respectively. Screws 37 are threaded into the vertebrae through apertures 80 and apertures 36 and 58, fixing components 22 and 24 to their respective vertebrae. Apertures 80 of prosthesis engaging portion 76 are sized slightly larger than the heads of the bone screws 37 used to attach components 22 and 24 to their respective vertebrae. When all of the holes have been drilled and all of the screws have been threaded into the bone, clips 82 are disengaged from components 22 and 24 and insertion tool 70 is removed. Similarly, in the embodiment of insertion tool 70 illustrated in FIGS. 15a–15b having cam screws 90, components 22 and 24 are attached to prosthesis-engaging portion 76 by locking cam screws 90 into one each of apertures 36 and 58. Holes are drilled through apertures 80 and apertures 36 and 58 not occupied by cam screws 90. After such holes are drilled, screws are threaded into such vertebra holes. The cam screws are then unlocked, the insertion tool 70 is removed and the remaining holes are drilled through apertures 36 and 58 in components 22 and 24. Bone screws 37 are threaded into the vertebrae through components 22 and 24 to complete the fixation of components 22 and 24 to their respective vertebrae.

The devices and methods of the present invention are currently believed to be most useful in repairing vertebral joints in the cervical region. Nevertheless, it is believed that the devices and methods of the present invention could also be useful in repairing other spinal motion segments as well.

In the embodiments of ball component 22 and trough component 24 which include a locking screw aperture 38 and 60, respectively, fixation of joint prosthesis 20 is completed by threading a locking screw (not shown) into apertures 38 and 60. When components 22 and 24 of joint prosthesis 20 are satisfactorily fixed, the operation may be concluded.

The attachment of components 22 and 24 to vertebrae has been primarily described through use of bone screws fixing the components to the vertebrae. It is understood that alternative attachment structures or methods may be used, such as by stapling or by applying adhesive to vertebra engaging surfaces 32, 35, 54 and/or 57, so long as components 22 and 24 are firmly fixed to their respective vertebrae so as to withstand the stresses inherent in continual rotational and translational movements. Further, joint prosthesis 20, as well as the bone screws or other structures used to implant them within the body, are preferably made of biocompatible materials such as stainless steel, titanium, or other known biocompatible materials or their equivalents. Insertion tool 70 can be made of any appropriate material, although stainless steel is preferred.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method comprising the steps of:
    providing a two-part intervertebral joint prosthesis, at least one of said prosthesis parts having a vertebra engaging surface and an adjoining wedge surface that is non-parallel to said vertebra engaging surface;
    inserting said prosthesis parts into a disc space between two adjacent vertebrae so that each of said prosthesis parts is adjacent to one of the vertebrae; and
    fastening said prosthesis parts to their respective vertebrae,
    wherein distraction of said vertebrae occurs during said inserting step.

2. The method of claim 1, wherein said distraction is at least partially caused by said wedge surface.

3. A method comprising the steps of:
    providing a two-part intervertebral joint prosthesis, at least one of said prosthesis parts having a vertebra engaging surface and an adjoining wedge surface that is non-parallel to said vertebra engaging surface;
    inserting said prosthesis parts into a disc space between two adjacent vertebrae so that each of said prosthesis parts is adjacent to one of the vertebrae; and
    fastening said prosthesis parts to their respective vertebrae,
    wherein both of said prosthesis parts have a vertebra engaging surface and an adjoining wedge surface that is non-parallel to said vertebra engaging surface.

4. The method of claim 3, wherein distraction of said vertebrae occurs during said inserting step.

5. The method of claim 4, wherein said distraction is at least partially caused by said wedge surfaces.

6. A method of implanting a multi-part intervertebral joint prosthesis in a body, comprising the steps of:
    placing the prosthesis parts in a predetermined spatial relationship;
    inserting the prosthesis parts into a disc space between two adjacent vertebrae so that one of the prosthesis parts abuts one of the vertebrae and the other of the prosthesis parts abuts the other of the vertebrae and so that the predetermined spatial relationship of the prosthesis parts is maintained; and
    fastening the prosthesis parts to their respective vertebrae;
    wherein said placing step further includes the step of engaging the prosthesis parts to an insertion tool.

7. The method of claim 6, wherein said engaging step further includes the step of holding the prosthesis parts to the insertion tool by at least one clip.

8. The method of claim 6, wherein said engaging step further includes the step of holding the prosthesis parts to the insertion tool by at least one cam screw.

9. The method of claim 6, wherein said fastening step includes fastening the prosthesis parts to their respective vertebrae by a plurality of bone screws.

10. The method of claim 6, further comprising the step of providing a tool having an elongated handle portion, and a prosthesis engaging portion connected to said handle portion for holding the prosthesis parts.

11. The method of claim 10, wherein said tool includes means connected to said prosthesis engaging portion for retaining the prosthesis parts in engagement with said prosthesis engaging portion.

12. The method of claim 10, wherein said placing step comprises engaging said prosthesis parts to said tool.

13. The method of claim 12, wherein said inserting step comprises maneuvering said tool with said prosthesis parts engaged thereto.

14. A method of implanting a multi-part intervertebral joint prosthesis in a body, comprising the steps of:

placing the prosthesis parts in a predetermined spatial relationship;

inserting the prosthesis parts into a disc space between two adjacent vertebrae so that one of the prosthesis parts abuts one of the vertebrae and the other of the prosthesis parts abuts the other of the vertebrae and so that the predetermined spatial relationship of the prosthesis parts is maintained; and fastening the prosthesis parts to their respective vertebrae; wherein said fastening step includes fastening the prosthesis parts to their respective vertebrae by an adhesive.

15. A method comprising the steps of:

providing a two-part intervertebral joint prosthesis, the prosthesis parts each having a flange with at least one aperture therethrough;

placing the prosthesis parts in a predetermined spatial relationship;

inserting the prosthesis parts into a disc space between two adjacent vertebrae so that the flange of one of the prosthesis parts abuts one of the vertebrae and the flange of the other of the prosthesis parts abuts the other of the vertebrae and so that the predetermined spatial relationship of the prosthesis parts is maintained; and fastening the flanges of the prosthesis parts to their respective vertebrae; and providing an insertion tool having a plurality of apertures which communicate with the apertures of the flanges of the prosthesis parts, and wherein said placing step further includes the step of engaging the prosthesis parts to the insertion tool.

16. The method of claim 15, wherein said engaging step further includes the step of retaining the prosthesis parts to the insertion tool by at least one clip.

17. The method of claim 15, wherein said engaging step further includes the step of retaining the prosthesis parts to the insertion tool by at least one cam screw.

18. The method of claim 15, wherein said fastening step further includes the steps of:

placing a drill through an aperture of one of said prosthesis parts;

drilling a hole in the vertebra; and threading a bone screw into the hole in the vertebra through the aperture of said one of said prosthesis parts.

19. The method of claim 18, wherein said drill placing, drilling and threading steps are repeated for each aperture in each prosthesis part flange.

20. The method of claim 19, wherein each bone screw includes a head, and further including the step of threading a locking screw into each of the prosthesis parts so as to cover a portion of the head of each bone screw.

21. The method of claim 18, wherein said step of placing a drill includes placing the drill through an aperture of said insertion tool, and said step of threading a bone screw includes threading the bone screw through said aperture of said insertion tool.

22. The method of claim 15, wherein said fastening step includes fastening at least one of the prosthesis parts to a vertebra by an adhesive.

23. The method of claim 15, wherein said fastening step includes fastening at least one of the prosthesis parts to a vertebra by a bone screw.

24. A method comprising the steps of:

providing an intervertebral joint prosthesis having (1) a ball component for engagement with a first vertebra, said ball component including a generally convex surface, and a flange at one end of said ball component for engaging the first vertebra, and (2) a trough component for engagement with a second vertebra adjacent to the first vertebra, said trough component including a generally concave surface with a substantially flat portion, and a flange at one end of said trough component for engaging the second vertebra;

inserting said ball component into a disc space between two adjacent vertebrae so that said flange of said ball component abuts one of the vertebrae;

inserting said trough component into the disc space so that said flange of said trough component abuts the other of the vertebrae, and so that said substantially flat portion of said generally concave surface is adjacent to said generally convex surface; and fastening said ball component and said trough component to their respective vertebrae.

25. The method of claim 24, further comprising the steps of (1) providing a tool having an elongated handle portion and a prosthesis engaging portion connected to said handle portion, and (2) engaging said ball component and said trough component to said tool prior to said inserting steps.

26. The method of claim 25, wherein said tool further includes means connected to said prosthesis engaging portion for retaining the prosthesis in engagement with said prosthesis engaging portion.

27. The method of claim 25 wherein said inserting steps occur substantially simultaneously.

28. The method of claim 25 wherein said engaging step maintains said ball component and said trough component in a predetermined spatial relationship.

29. The method of claim 24 wherein said inserting steps are performed via an anterior F approach to the vertebrae.

30. The method of claim 24 wherein said fastening step includes fastening at least one of said ball component and said trough component to a respective vertebra by a bone screw.

31. The method of claim 24 wherein said fastening step includes fastening at least one of said ball component and said trough component to a respective vertebra by an adhesive.

32. A method of implanting a multi-part intervertebral joint prosthesis in a body, comprising the steps of:

placing the prosthesis parts in a predetermined spatial relationship;

inserting the prosthesis parts into a disc space between two adjacent vertebrae so that one of the prosthesis parts abuts one of the vertebrae and the other of the prosthesis parts abuts the other of the vertebrae and so that the predetermined spatial relationship of the prosthesis parts is maintained, wherein said inserting step causes distraction of the vertebrae; and fastening the prosthesis parts to their respective vertebrae.

33. The method of claim 32, further comprising the steps of:

providing a wedge surface on at least one of said prosthesis parts such that said wedge surface causes said distraction of the vertebrae during said inserting step.

* * * * *